(12) United States Patent
Melyukov et al.

(10) Patent No.: US 9,194,693 B2
(45) Date of Patent: Nov. 24, 2015

(54) CONTACTLESS METHOD FOR DETERMINING THE RAY OF A BEAM, CORRESPONDING SYSTEM

(71) Applicant: Commissariat à l'Energie Atomique et aux Energies Alternatives, Paris (FR)

(72) Inventors: Dmitry Melyukov, Paris (FR); Pierre-Yves Thro, Paris (FR)

(73) Assignee: COMMISSARIAT A L'ENERGIE ATOMIQUE ET AUX ENERGIES ALTERNATIVES (FR)

( * ) Notice: Subject to any disclaimer, the term of this patent is extended or adjusted under 35 U.S.C. 154(b) by 0 days.

(21) Appl. No.: 14/349,181
(22) PCT Filed: Oct. 2, 2012
(86) PCT No.: PCT/EP2012/069456
§ 371 (c)(1),
(2) Date: Jul. 21, 2014
(87) PCT Pub. No.: WO2013/050366
PCT Pub. Date: Apr. 11, 2013

(65) Prior Publication Data
US 2014/0365168 A1    Dec. 11, 2014

(30) Foreign Application Priority Data
Oct. 3, 2011    (FR) ..................................... 11 58904

(51) Int. Cl.
*G01B 11/08*    (2006.01)
*G01J 1/42*    (2006.01)
*G01B 17/00*    (2006.01)
*G01N 25/02*    (2006.01)

(52) U.S. Cl.
CPC ................ *G01B 11/08* (2013.01); *G01B 17/00* (2013.01); *G01J 1/4257* (2013.01); *G01N 25/02* (2013.01)

(58) Field of Classification Search
CPC . G01N 21/17; G01N 21/171; G01N 21/1717; G01N 21/1731; G01N 21/71

USPC ......................................................... 702/157
See application file for complete search history.

(56) References Cited

U.S. PATENT DOCUMENTS

| 4,336,597 | A | * | 6/1982 | Okubo et al. | .................. 702/157 |
| 4,675,528 | A | * | 6/1987 | Langner et al. | ........... 250/396 R |
| 7,420,146 | B1 | | 9/2008 | Spawr | |
| 2004/0218186 | A1 | | 11/2004 | Viol | |

FOREIGN PATENT DOCUMENTS

FR    2980846 A2 *    4/2013    ............. G01B 21/02

OTHER PUBLICATIONS

International Search Report for PCT/EP2012/069456 mailed Nov. 14, 2012.
English Translation of the Written Opinion for PCT/EP2012/069456.

* cited by examiner

*Primary Examiner* — Mischita Henson
(74) *Attorney, Agent, or Firm* — Lerner, David, Littenberg, Krumholz & Mentlik, LLP

(57) ABSTRACT

The invention relates to a method for measuring a ray r0 of a radiation beam (20), characterized in that it comprises the steps according to which a source (2) of a radiation beam (20) excites (S1) a standard member (1) via heat, in a periodic manner at a frequency (f), thereby obtaining a periodic thermal excitation of the standard member (1); a sensor (3) measures (S2) a periodic thermal response on the part of the standard member, in response to the periodic thermal excitation; a processor (4) determines (S3) a phase shift (φ) between the periodic thermal excitation and the periodic thermal response; the source (2) exciting the standard member for a plurality of frequencies (f) and the processor (4) determining a phase shift for each frequency (f), and thereby determining a plurality of phase shifts (φ); the processor (4) determines (S4) a minimum φ min of the phase shift (φ) thanks to the plurality of phase shifts determined in this manner, and determines (S5) the ray r0 of the beam (20) via the following formula: $r0 = \Delta/g(\phi_{min})$ where $\Delta$ is the thickness of the standard member (1) and where g is a function dependent on the type of heat radiation beam (20).

6 Claims, 9 Drawing Sheets

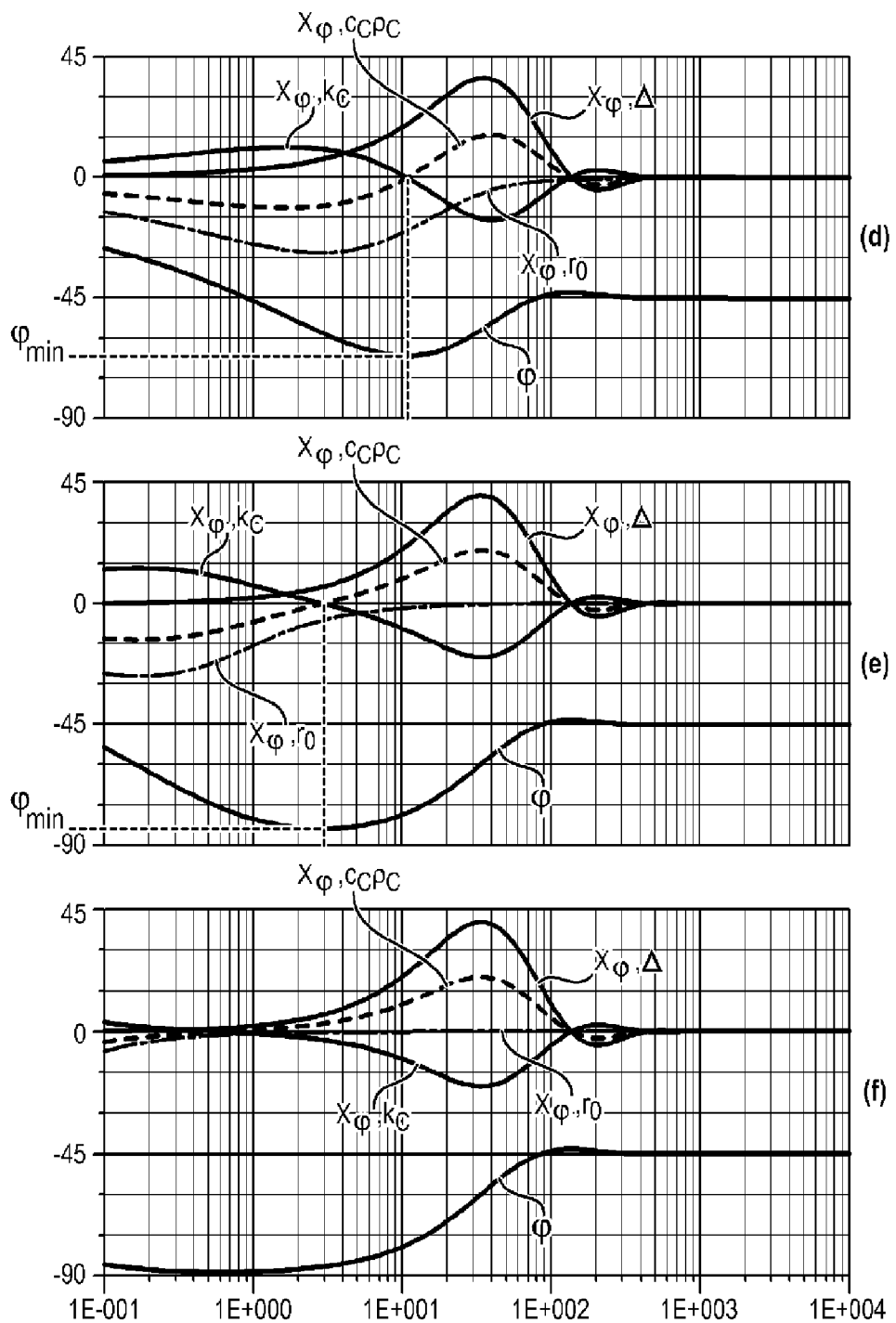

Figure 1:
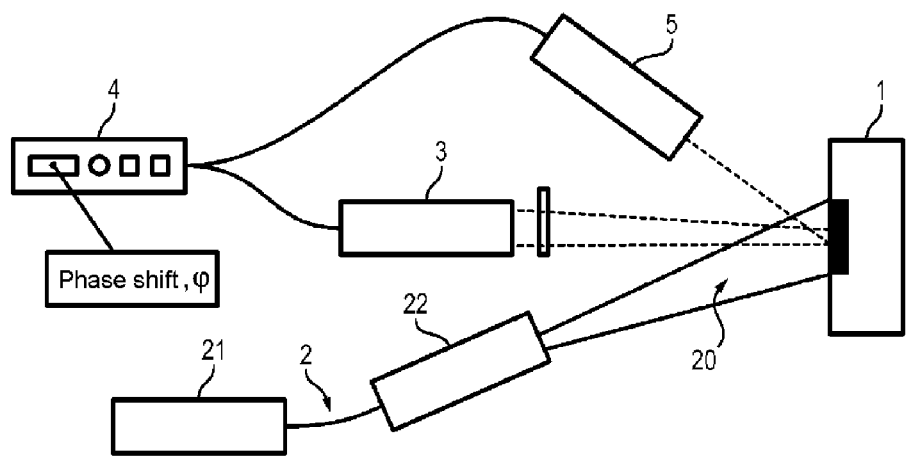

CONTACTLESS METHOD FOR DETERMINING THE RAY OF A BEAM, CORRESPONDING SYSTEM

CROSS-REFERENCE TO RELATED APPLICATION

The present application is a national phase entry under 35 U.S.C. §371 of International Application No. PCT/EP2012/069456 filed Oct. 2, 2012, which claims priority from French Patent Application No. 1,158,904 filed Oct. 3, 2011, the disclosures of which are hereby incorporated herein by reference.

GENERAL TECHNICAL FIELD

The present invention relates to a method for measuring a radius of a radiation beam.

It also relates to a system for applying the method.

STATE OF THE ART

Methods are known for measuring radii of radiation beams (and therefore the diameters), for example, by using cameras or mechanical systems associated with the power measurement systems.

However, these methods require expensive optical equipment and/or are generally long to apply. Further, the sensors of the cameras, for example, have rather small dimensions of the order of a few millimeters and do not give the possibility of conducting measurements on beams of large sizes.

PRESENTATION OF THE INVENTION

The invention proposes to overcome at least one of these drawbacks.

For this purpose, a method for measuring a radius r0 of a radiation beam is proposed according to the invention, characterized in that it includes steps according to which a source of a radiation beam excites a standard member via heat, periodically at a frequency, in order to obtain a periodic thermal excitation of the standard member;

a sensor measures a periodic thermal response of the standard member as a response to the periodic thermal excitation;

a processor determines a phase shift between the periodic thermal excitation and the periodic thermal response.

The source exciting the standard member for a plurality of frequencies and the processor determining a phase shift for each frequency, and thus determining a plurality of phase shifts;

the processor
determines a phase shift minimum $\phi_{min}$ by means of the thereby determined plurality of phase shifts, and
determines the radius r0 of the beam with a formula of the type:

$$r0 = \Delta / g(\phi_{min})$$

wherein $\Delta$ is the thickness of the standard member, and
g is a function which depends on the type of heat radiation beam.

The invention is advantageously completed by the following characteristics, taken alone or in any of their technically possible combinations:

the function g is of the polynomial type, the coefficients of the polynomial depending on the type of heat radiation beam;

the processor determines the radius r0 of the beam, in mm, with the formula:

$$r0 = (100 \cdot \Delta)/(0.227 \cdot \phi_{min}^3 + 57.856 \cdot \phi_{min}^2 + 5688.2 \cdot \phi_{min} + 208620)$$

wherein $\Delta$ is the thickness of the standard member, in μm.

when the heat radiation beam is of the uniform type, the processor determines the radius r0 of the beam in mm, with the formula:

$$r0 = \Delta/(0.0032\phi_{min}^3 + 0.7405\phi_{min}^2 + 64.894\phi_{min} + 2163.3)$$

for $(1.68 < r_0/\Delta < 100)$;

$$r0 = \Delta/(6E\text{-}05\,\phi_{min}^4 + 0.0196\phi_{min}^3 + 2.2587\phi_{min}^2 + 125.58\phi_{min} + 3046)$$

for $(1.68 < r_0/\Delta < 20)$; and $$r0 = \Delta/(2E\text{-}06\phi_{min}^5 + 0.0007\phi_{min}^4 + 0.0947\phi_{min}^3 + 6.8299\phi_{min}^2 + 261.57\phi_{min} + 4627.7)$$

for $(1.68 < r_0/\Delta < 100)$
wherein $\Delta$ is a thickness of the standard member in μm.

the source excites the standard member in a sinusoidal periodic manner;
one has the relationship:

$$1.5 \cdot \Delta \leq r0 \leq 20 \cdot \Delta.$$

The invention also relates to a system for applying the method.

The invention has many advantages.

It allows the measurement of the radii of the radiation beams (and therefore determination of the diameters of the beams) with an inexpensive equipment in a simple and rapid way.

The invention only requires that the thickness of the standard member should be accurately known, without knowing its thermal conductivity, its heat capacity or its density.

The standard member may be of any shape, for example a tube or a plate, and in any homogeneous material, and therefore should not necessarily have any particular electric and/or magnetic conductivity, optical transparency or acoustic impedance characteristics.

One of the conditions of the measurement is that the standard member should be in a fluid or laid on a not very thermally conductive substrate or, more specifically, be surrounded by a transparent medium which has an effusivity (effusivity is a quantity which takes into account the capability of a body or of a medium of changing temperature when it receives a supply of thermal energy and is expressed in $W \cdot s^{0.5}/m^2 \cdot K$) much less than that of the standard member (for example air). This condition is however not restrictive.

PRESENTATION OF THE FIGURES

Figure 2:
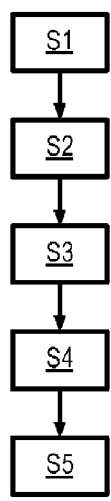
Figure 3:
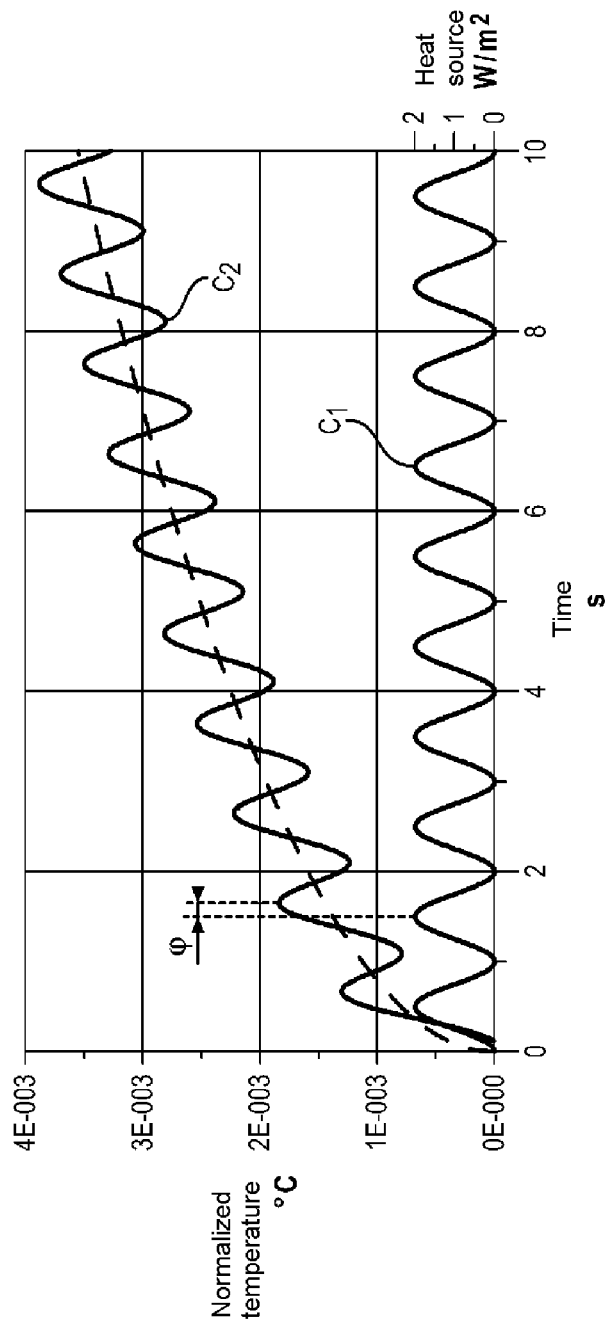
Figure 4:
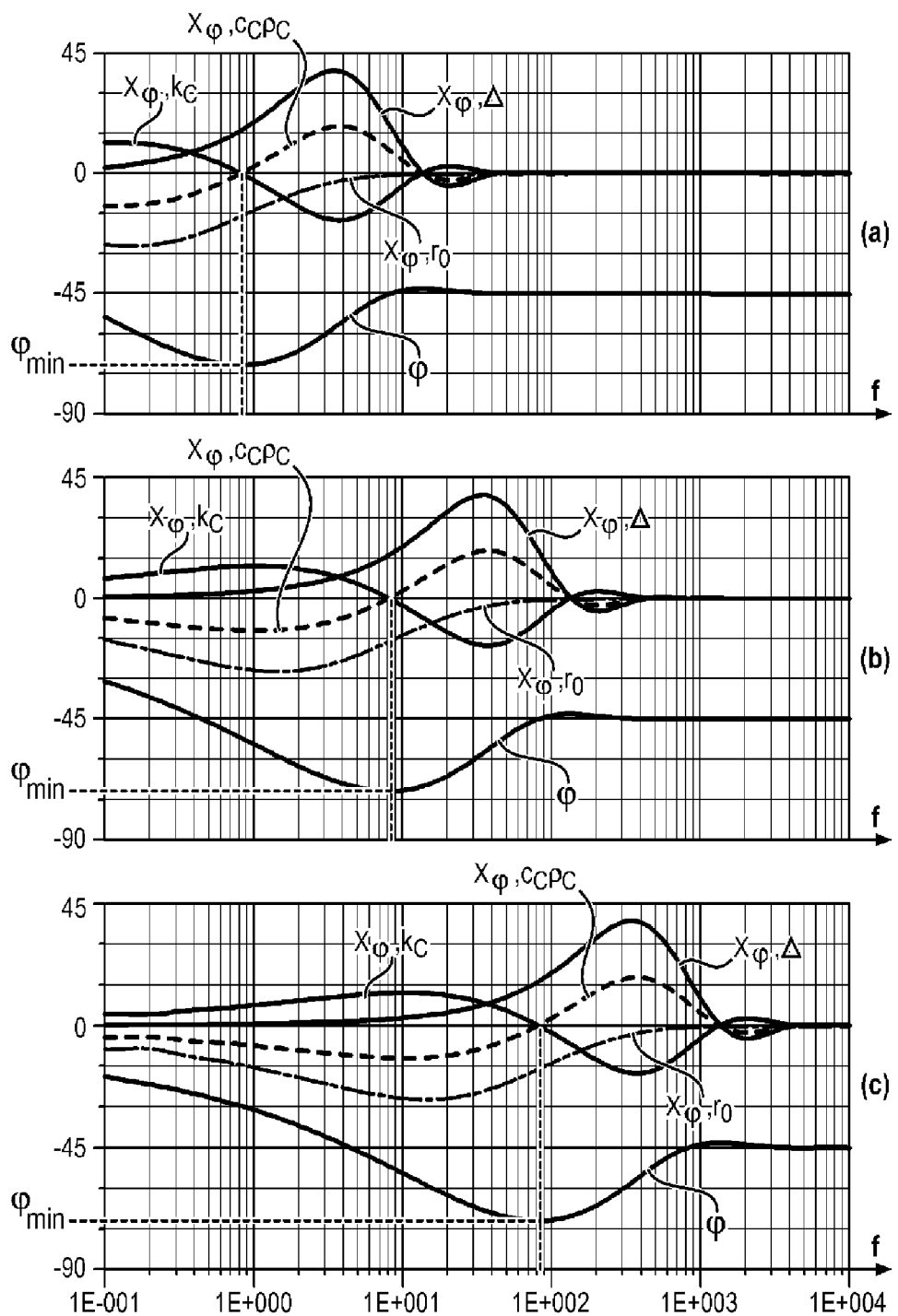
Figure 5:
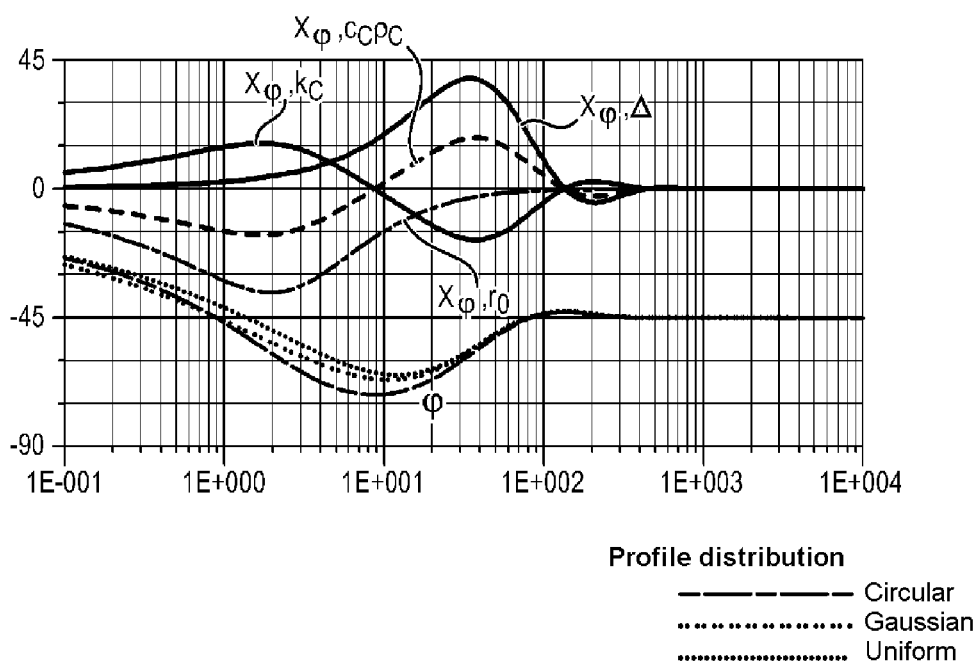
Figure 6:
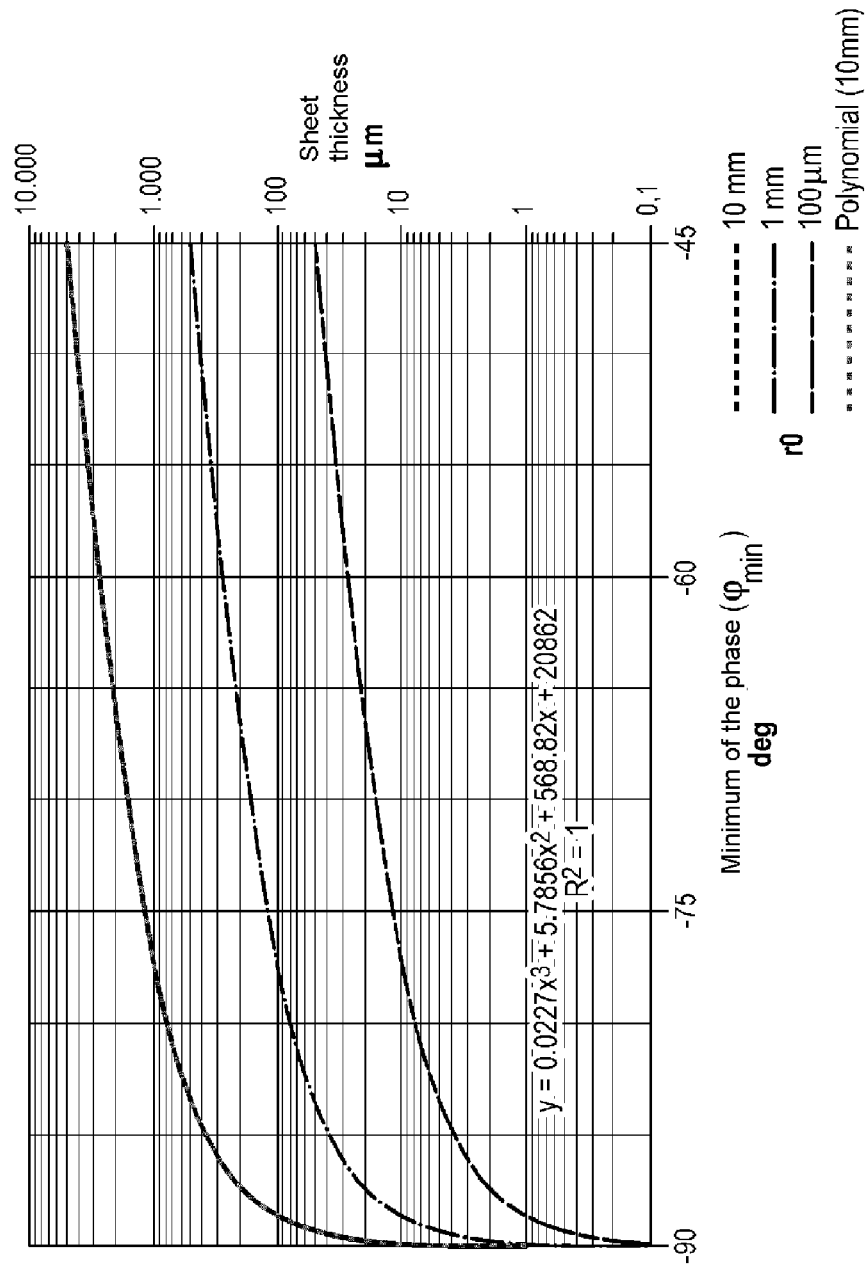
Figure 7:
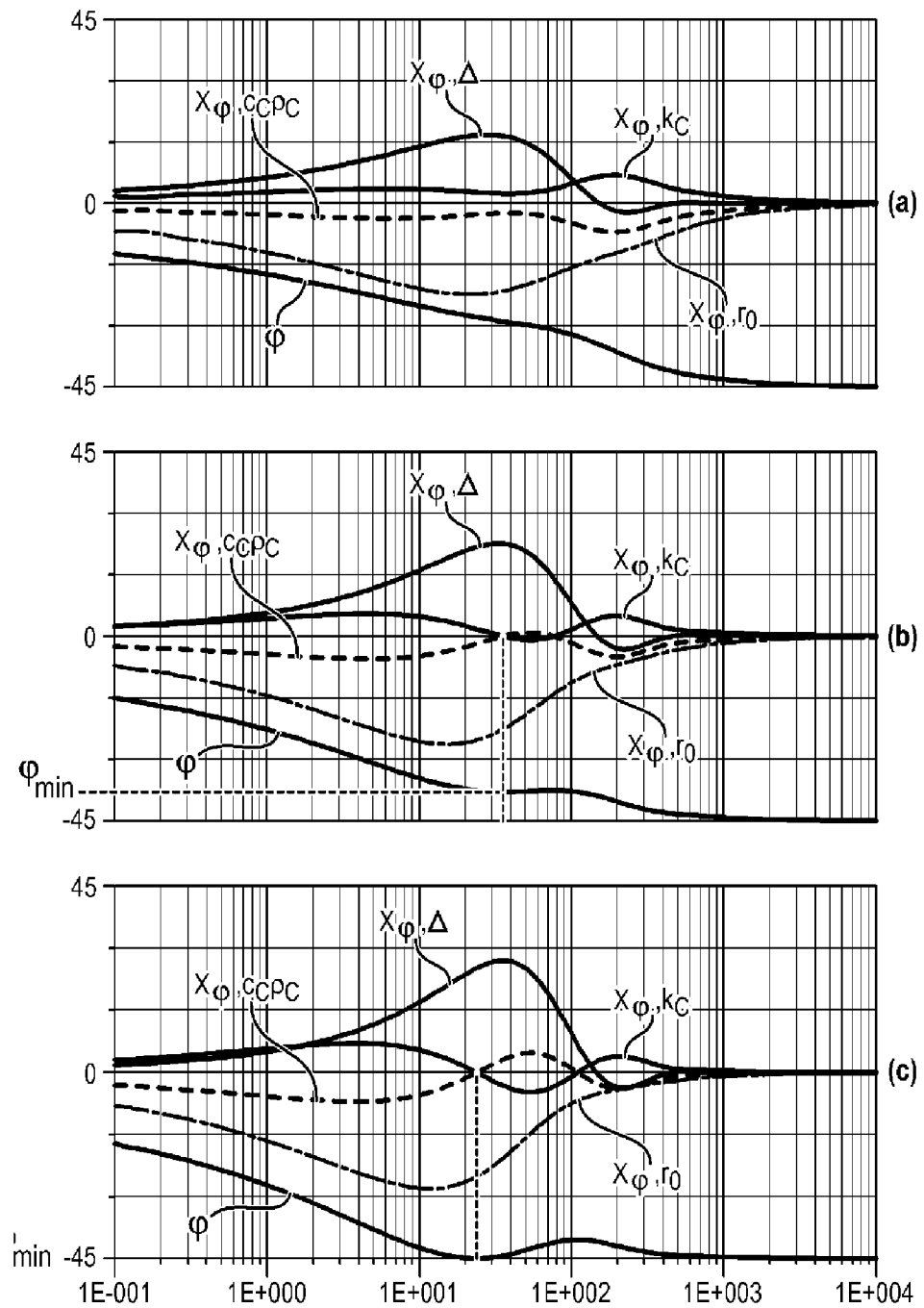
Figure 8:
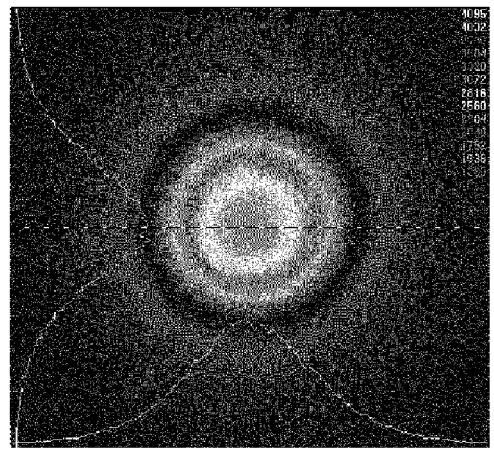
Figure 9A:
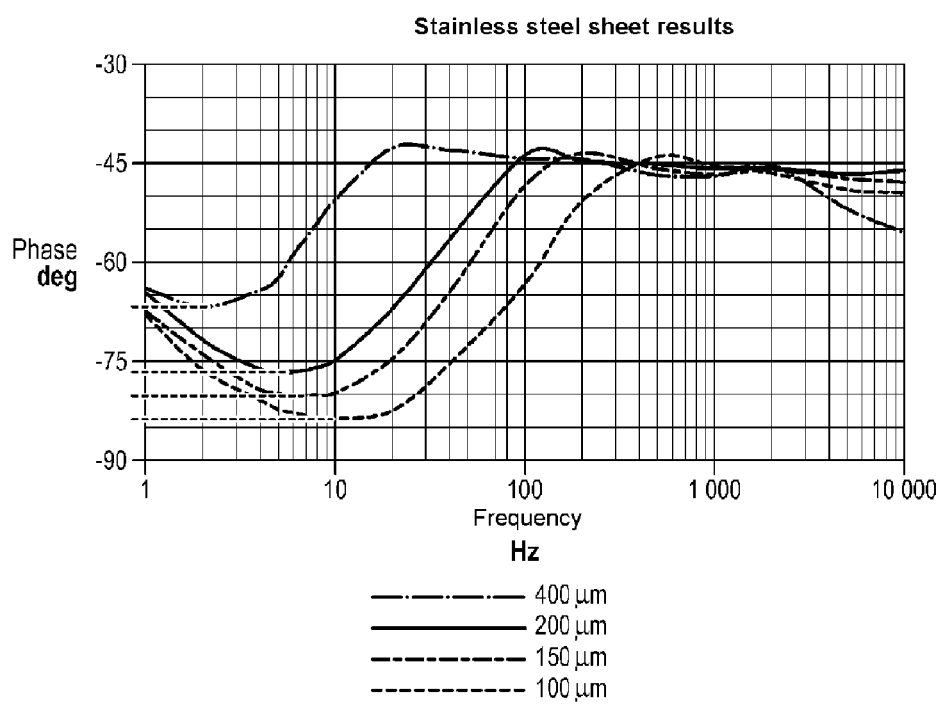
Figure 9B:
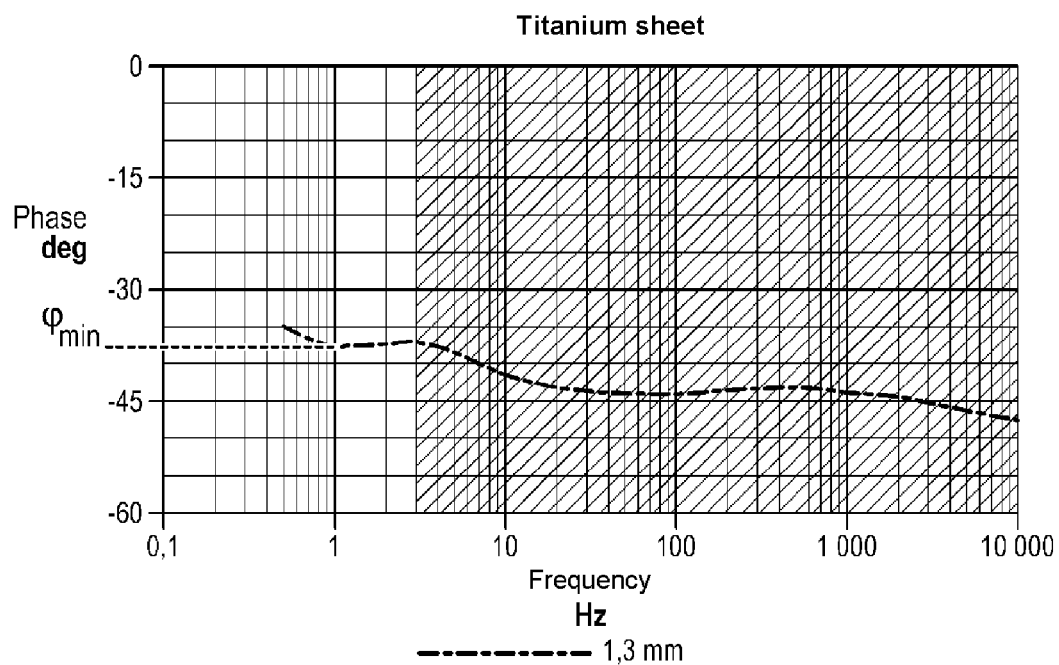
Figure 9C:
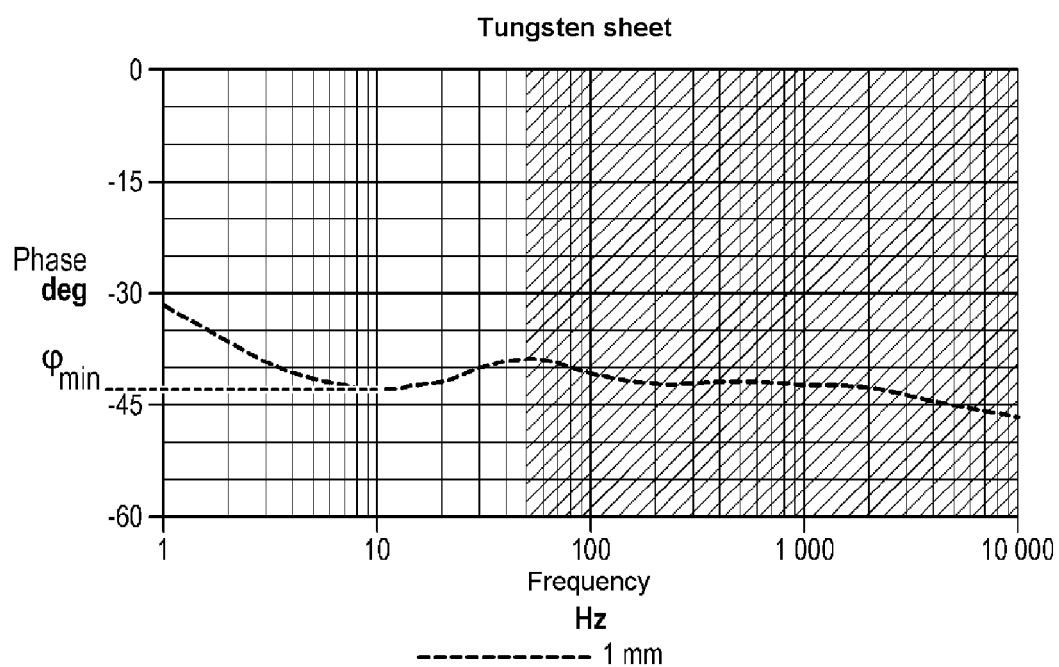

Other features, objects and advantages in the invention will become apparent from the description which follows, which is purely illustrative and nonlimiting and which should be read with reference to the appended drawings wherein:

FIG. 1 schematically illustrates a possible system for applying a method according to the invention, for measuring a radius of a beam, FIG. 2 schematically illustrates main steps of a method for measuring a radius of a beam according to the invention;

FIG. 3 illustrates a curve of the surface temperature of the standard member subject to periodic thermal excitation;

FIG. 4 illustrates the influence of thermal diffusivity on the minimum of a phase shift and on sensitivity coefficients, for a sheet with a thickness of 300 μm for a beam size $r_0 = 3$ mm, FIG. 4 (a): diffusivity equal to 0.1 [$\times 10^{-5} m^2/s$], FIG. 4(b): diffusivity equal to 1 [×10⁻⁵m²/s], and
FIG. 4(c): diffusivity equal to 10 [×10⁻⁵m²/s];
FIG. 5 illustrates the influence of the spatial distribution of the energy of the laser beam on the minimum of a phase shift and on sensitivity coefficients, for a sheet with a thickness of 600 µm for a beam size $r_0$=3 mm;
FIG. 6 illustrates a nomogram of the thickness of the standard member versus the phase shift minimum for different values of the radius of the heat beam;
FIG. 7 illustrates the influence of the ratio $r_0/\Delta$ on the phase shift minimum and on sensitivity coefficients for a sheet with the thickness of 300 µm and a thermal diffusivity of $10^{-5}$ m²/s
FIG. 7(a): ratio $r_0/\Delta$ equal to 1;
FIG. 7(b): ratio $r_0/\Delta$ equal to 1.5;
FIG. 7(c): ratio $r_0/\Delta$ equal to 2;
FIG. 7(d): ratio $r_0/\Delta$ equal to 5;
FIG. 7(e): ratio $r_0/\Delta$ equal to 20;
FIG. 7(f): ratio $r_0/\Delta$ equal to 100;
FIG. 8 illustrates a Gaussian distribution of the energy in the heat beam; and
FIGS. 9A, 9B and 9C show phase shift measurements of the thermal response versus the excitation frequency, for standard members in stainless steel, in titanium and in tungsten, respectively.
In the whole of the figures, similar elements bear identical numerical references.

DETAILED DESCRIPTION

FIG. 1 schematically illustrates a possible system for applying a method according to the invention, for a measurement of a radius r0 of a beam 20 by means of a standard member 1 for which the thickness Δ is accurately known, a method for which the main steps are schematically illustrated in FIG. 2.

The standard member 1 is of any shape, for example a tube or a plate, and may be in any homogeneous material (i.e. a noncomposite material). The material should not necessarily have particular electric and/or magnetic conductivity, acoustic impedance or optical transparency characteristics (it is understood that, in spite of this, it should be absorbent at the excitation wavelength). The material may for example be in a non-limiting way, stainless steel, aluminium, titanium, tungsten or an alloy of the aforementioned metals, or carbon.

The standard member 1 may be in a thermally not very conductive fluid or laid on a thermally not very conductive substrate or, more specifically be surrounded by a transparent medium and which has much less effusivity than that of the layer (for example air). Typically, the ratio of the effusivities between the standard member 1 and the not very conductive medium should be of the order of 1,000.

The system mainly includes:
a source 2 of a radiation beam 20 for which the radius r0 is to be determined (the beam 20 should be able to heat the standard member 1 and the standard member is therefore opaque to the wavelength of the beam 20 used);
a sensor 3 for a thermal response from the standard member, in response to the thermal excitation; and
a processor 4.

The source 2 may be any source of the radiation beam 20 but in order that the measurement of its radius r0 should be possible, the beam 20 should be able to heat the standard member 1. As a nonlimiting example, the source 2 may be a laser of a laser diode.

The distribution of the energy E(r) in the beam 20 may for example be:
circular, i.e.

$$E(r) = \left(1 - \frac{r}{2r0}\right)^2 \cdot \left(1 + \frac{r}{2r0}\right)^2, 0 < r < 2r0$$

wherein r0 is the radius of the beam 20,
Gaussian, i.e.

$$E(r) = e^{-\left(\frac{r}{r_0}\right)^2},$$

or
uniform, i.e.

$$E(r)=1, 0<r<r0$$

As this will be seen in more detail in the continuation of the present description, the source 2 is modulated in order to excite the standard member periodically, for example, in a sinusoidal manner. The modulation may be generated by a system outside the source 2, for example a mechanical chopper if the source 2 is continuous.

In response to the excitation, the standard member 1 has a thermal response, the sensor 3 being suitable for measuring the thermal response. The sensitivity peak of the sensor 3 depends on a temperature at which the measurement is conducted.

The thermal response of the standard 1 may thus be, in a non limiting way:
a thermal expansion of the standard member 1,
a change in reflectance of a surface of the standard member 1, i.e. the ratio of the reflected energy over the incident energy, generally expressed in decibels or as a percentage;
a change in the emissivity of the standard member, i.e. the ratio between the energy which it radiates and that which a black body would radiate at the same temperature, a ratio comprised between 0 and 1;
a change in the luminance, i.e. the light intensity calculated relatively to a given surface (m²), generally expressed in candelas per square meter (cd/m²);
et cetera.

As a nonlimiting example, in order to measure thermal expansion of the standard member and/or a change in the reflectance of a surface of the standard member and/or a change in the luminance of the standard member, the sensor may be an optical or acoustic sensor.

The example of FIG. 1, which is nonlimiting, describes an optical sensor 3 measuring a thermal response consisting in a change in the luminance of the standard member 1. The sensor 3 is thus a HgCdZnTe sensor, sensitive between 2 and 11 µm (mid-infrared), since the measurements are conducted for temperatures comprised between 20° C. and a few hundred degrees Celsius (typically 200° C.). In FIG. 1, the sensor 3 is a sensor of the VIGO brand with a spectral bandwidth of 3-11 µm with a response time of 7 ns.

The processor 4 conventionally includes all the memory storage, processing and computing means for applying a method according to the invention. It may notably include a synchronous detection amplifier, known per se to one skilled in the art, for measuring a phase shift as this will be seen in more detail in the continuation of the present description. Computer means other than the synchronous detection amplifier are of course possible.

In order to be able to measure the phase shift between a thermal excitation of the standard member 1 and a thermal response of the standard member 1 to the excitation, the processor 4 is connected to the sensor 3 on the one hand and to an auxiliary sensor 5 on the other hand, directly observing the excitation of the standard member 1. The sensor 5 is advantageously a silicon photodiode. By directly observing the excitation of the standard member 1 with the auxiliary sensor 5, it is possible to avoid the necessity of taking into account a parasitic phase shift due to the source 2 in the calculations for measuring the thickness. The aforementioned parasitic phase shift may for example be due to
- a phase shift between an electric signal of a generator 21 of the source 2 and an emission of the beam 20 by a laser 22 of the source 2;
- a phase shift between the emission of the beam 20 by the laser 22 of the source and an actual excitation of the standard member 1,
- et cetera.

It is understood that the processor 4 may also be connected to the source and not to an auxiliary sensor if the phase shift due to the source 2 is taken into account in the calculations for measuring the thickness.

According to a possible method for measuring the radius r0 of the beam 20, during a step S1, the source 2 excites the standard member 1 periodically by means of the beam 20, in order to obtain a periodic thermal excitation of the standard member 1, via heating.

As shown by the curve C1 of FIG. 3, the periodic excitation is effected for example in a sinusoidal way, but it may also be a periodic, square wave excitation for example, or other excitation. The curve C1 of FIG. 3 is plotted for an excitation frequency f of one second for example.

As this may be seen on curve C2 of FIG. 3, during a step S2, the sensor 3 measures a periodic thermal response of the standard member 1, in response to the periodic thermal excitation. The thermal response is for example here the change in the luminance of the standard member due to the change in temperature of the standard member 1.

During step S3, the processor 4 experimentally determines a phase shift $\phi$ between the periodic thermal excitation and the periodic thermal response, i.e. the gap for example between a top of the curve C1 and a corresponding top of the curve C2.

The source 2 excites the standard member 1 for a plurality of frequencies f (typically about 15 frequencies, the frequencies being for example comprised between 1 Hz and 10 kHz, depending on the standard member 1) and the processor 4 determines a phase shift for each excitation frequency f, and thereby determining a plurality of phase shifts $\phi$.

During a step S4, the processor 4 determines a minimum $\phi_{min}$ of the phase shift $\phi$ by means of the thereby determined plurality of phase shifts. The $\phi_{min}$ interpolation method from the plurality of phase shifts determined by the processor 4, and used for obtaining the minimum $\phi_{min}$, is known to one skilled in the art, for example, a polynomial or other interpolation.

The determination of $\phi_{min}$ is important for determining the radius r0.

The inventors have actually discovered, as shown in FIG. 4, in a quite unexpected way, that the value of $\phi_{min}$ is independent of the changes in the thermal properties of the standard member, and allows determination of the radius r0, as explained hereafter.

Preliminary Step

FIG. 4 resumes the curve of the phase $\phi(f)$, with equation (E1), known to one skilled in the art:

$$\varphi(f) = \arg \int_0^\infty \frac{0.5\xi \cdot e^{-0.25\xi^2}}{\left(\frac{\xi}{r_0}\right)^2 - i2\pi f \frac{C_c \rho_c}{k_c} - \alpha^2} \times A \cdot d\xi$$

wherein $$A = \left[ \frac{2\alpha \cdot e^{-\kappa_1 \Delta}}{\kappa_1 D} \left\{ \begin{array}{l} (e^{-\alpha \Delta} - e^{-\kappa_1 \Delta})(1 + R k_S \kappa_2) + \\ \left(e^{-\kappa_1 \Delta} - \frac{\kappa_1}{\alpha} e^{-\alpha \Delta}\right) \frac{k_S \kappa_2}{k_C \kappa_1} \end{array} \right\} + \left(1 - \frac{\alpha}{\kappa_1}\right) \right]$$

and wherein $$D = (1 + e^{-2\kappa_1 \Delta}) \frac{k_S \kappa_2}{k_C \kappa_1} + (1 - e^{-2\kappa_1 \Delta})(1 + R k_S \kappa_2),$$

$$\kappa_1 = \sqrt{\left(\frac{\xi}{r_0}\right)^2 - i2\pi f \frac{C_c \rho_c}{k_c}},$$

$$\kappa_2 = \sqrt{\left(\frac{\xi}{r_0}\right)^2 - i2\pi f \frac{C_s \rho_s}{k_s}}$$

wherein
 ξ—independent variable,
 c—mass heat capacity, [J/kg·K],
 ρ—density [kg/m³],
 k—thermal conductivity [W/m·K],
 R—possible thermal resistance between the standard member and the medium [m$^{2K \cdot W-1}$],
 α—absorption coefficient of the standard member at the excitation wavelength, [m$^{-1}$], and
wherein
 the indices c and s correspond to the standard member and to the medium respectively.

In order to better understand how each parameter influences the curve of the phase $\phi(f)$ of FIG. 4 (and accordingly the possibility of extracting these parameters from this curve), it is proceeded with a numerical analysis of sensitivity for each of said thermophysical parameters of the standard member 1.

Reduced sensitivity coefficients X are defined, and obtained by modeling:

$$X_{\varphi, \chi} = \chi \frac{\partial \varphi}{\partial \chi}$$

Each sensitivity coefficient X shows how the phase $\phi$ is modified for a given relative variation of the parameter $\chi$. It is actually understood that it is only possible to identify a parameter $\chi$ if the phase $\phi$ is sensitive to its variation.

The sensitivity coefficients X are also plotted in FIG. 4 for the following $\chi$ parameters:
 the thickness $\Delta$ of the standard member 1;
 the radius r0 of the heat radiation beam 20;
 the thermal conductivity kc of the standard member 1; and
 the heat capacity $c_c \rho_c$ of the standard member 1.

The curves of FIG. 4 have thus been plotted with different numerical values of the thermal diffusivity of the standard member for example, i.e. the physical quantity which characterizes the capability of the standard member of transmitting heat from one point to another of the latter by conduction; the thermal diffusivity is equal to the ratio of the thermal conductivity over the bulk heat capacity and is expressed in m²/s and is generally noted as a. In FIG. 4, the thermal diffusivity assumes the values $0.1 \times 10^{-5}$ m²/s (FIG. 4(a)), $1 \times 10^{-5}$ m²/s (FIG. 4(b) and $10 \times 10^{-5}$ m²/s (FIG. 4(c)).

In FIG. 4, it is seen that the change in the thermal properties of the standard member 1, in the form of the thermal diffusivity, indeed causes translation of the phase shift curve cp into the domain of higher frequencies when diffusivity increases, but the phase shift minimum $\phi_{min}$ remains always independent of thermal diffusivity and always has the same value.

It is further seen that for the value of the excitation frequency giving $\phi_{min}$, the sensitivity coefficients $X\phi,kc$ and $X\phi,c_c\rho_c$ become zero, i.e. at this frequency, the phase does neither depend on the thermal conductivity kc of the standard member 1 nor on the peak capacity $c_c\rho_c$ of the standard member 1. On the other hand, for this value of the excitation frequency, $\phi_{min}$ depends on the thickness $\Delta$ of the standard member 1 and on the radius r0 of the heat radiation beam 20 (since the corresponding sensitivities are nonzero and are in fact correlated: this means that the value $\phi_{min}$ depends on the ratio $\Delta/r_0$). As shown in FIG. 5, the excitation frequency giving the minimum $\phi_{min}$ and its absolute value indeed vary according to the shape of the beam (for an energy distribution in the beam which is circular, Gaussian or uniform, respectively) but remain independent of diffusivity (since the corresponding sensitivities $X\phi,kc$ and $X\phi,c_c\rho_c$ are nonzero).

In other words, as the thickness $\Delta$ is known, it is possible to determine from $\phi_{min}$, the value of the radius r0 of the beam 20, and this without knowing the thermal conductivity kc of the standard member 1 or its heat capacity $c_c\rho_c$.

Now, there is no analytical formula which directly gives the value of the radius r0 of the beam 20 as a function of:
the phase shift minimum $\phi_{min}$, and of
the thickness $\Delta$.

Consequently, during a preliminary step for the method, a plurality of curves according to FIG. 4 is therefore plotted, from numerical calculations in accordance with (E1), for different numerical values of the thickness $\Delta$ and of the radius $r_0$.

From the plurality of the thereby obtained numerical $\phi_{min}$ values, the curves of FIG. 6 are plotted again taking the value of the thickness A according to each obtained numerical $\phi_{min}$ for example for three numerical values of the radius r0 of the Gaussian heat beam 20, i.e. 10 mm, 1 mm and 100 µm respectively (it is recalled here that for a different spatial distribution of the beam, the curves would be different).

It is seen that the curves of FIG. 6, obtained numerically, are parallel for the different values of $r_0$, and it is inferred therefrom that the phase $\phi_{min}$ depends on the ratio $\Delta/r_0$.

The curves of FIG. 6 are obtained numerically, but it is possible, also during the aforementioned preliminary step, to find an analytic function g which approximates one of said curves obtained numerically, as shown by the dotted line curve of FIG. 6 (example of a polynomial approximation of degree 3 for approximating the curve plotted for r0 equal to 10 mm).

An approximate function, $g(\phi_{min})$, is thereby determined from one of the numerical curves of FIG. 6, such that:

$$\Delta/r_0 = g(\phi_{min}),$$

wherein g is a function which depends on the heat radiation beam 20 type.

The function g may assume any analytical approximation form for one of the curves of FIG. 6. Preferentially, but not as a limitation, the function g is of the polynomial type (see FIG. 6), the coefficients of the polynomial depending on the type of heat radiation beam 20. The degree of the polynomial may be any degree (the greater the ratio r0/$\Delta$, the more it is necessary to use a polynomial with a high degree in order to obtain good accuracy), for example, 5, 4 or 3.

This approximation g may thus be made for example by means of a formula of the type (polynomial of degree 3):

$$\Delta/r0 = (\alpha \cdot \phi_{min}^3 + \beta \cdot \phi_{min}^2 + \gamma \cdot \phi_{min} + \delta)$$

wherein the quadruplet ($\alpha, \beta, \gamma, \delta$) depends on the heat radiation beam type, $\Delta$ being expressed in µm and r0 in mm.

For example, when the heat radiation beam 20 is of the Gaussian type, and as shown in FIG. 6, g is given by the formula:

$$\frac{\Delta}{r0} = \frac{1}{100} \cdot (0.277 \cdot \varphi_{min}^3 + 57.856 \cdot \varphi_{min}^2 + 5688.2 \cdot \varphi_{min} + 208620)$$

According to another example, when the heat radiation beam 20 is of the uniform type:

$$\Delta/r0 = (0.0032\phi_{min}^3 + 0.7405\phi_{min}^2 + 64.894\phi_{min} + 2163.3)$$

for $(1.68 < r_0/\Delta < 10)$ $$\Delta/r0 = (6E\text{-}05\phi_{min}^4 + 0.0196\phi_{min}^3 + 2.2587\phi_{min}^2 + 125.58\phi_{min} + 3046)$$

for $(1.68 < r_0/\Delta < 20)$ $$\Delta/r0 = (2E\text{-}06\phi_{min}^5 + 0.0007\phi_{min}^4 + 0.0947\phi_{min}^3 + 6.8299\phi_{min}^2 + 261.57\phi_{min} + 4627.7)$$

for $(1.68 < r_0/\Delta < 100)$

The determination of the approximate function g from one of the curves of FIG. 6 is performed during a step prior to carrying out the method (for example before step S1), but does not correspond to a calibration step relatively to the standard member like in the prior art.

Indeed, the curves of FIG. 4 are obtained numerically from the relationship (E1), and the curves of FIG. 6, again taking the numerical values of $\phi_{min}$, are, as this has been seen, independent of the characteristics of the material of the standard member 1.

Producing the curves of FIG. 4, those of FIG. 6 and determining g by interpolation may be carried out by conventional processing and computing means, for example but not necessarily the processor 4.

After having described above the preliminary step for determining g, we resume the course of describing an example of a method according to the invention.

Once it has experimentally determined $\phi_{min}$ during step S4, by means of the plurality of phase shifts cp on the standard member 1, the processor 4 may therefore then determine, during step S5, the radius r0 by a formula of the type:

$$r0 = \Delta/g(\phi_{min})$$

With the preceding examples, when the heat radiation beam 20 is of a Gaussian type, the processor 4 determines, during step S5, the radius r0 in mm, with the formula:

$$r0 = 100 \cdot \Delta/(0.227 \cdot \phi_{min}^3 + 57.856 \cdot \phi_{min}^2 + 5688.2 \cdot \phi_{min} + 208620)$$

wherein $\Delta$ is the thickness of the standard member 1, in µm.

Also, when the heat radiation beam is of the uniform type, the processor 4 determines the radius r0 in mm with the formula:

$$r0=\Delta/(0.0032\phi_{min}^3+0.7405\phi_{min}^2+64.894\phi_{min}+2163.3)$$

for $(1.68<r_0/\Delta<10)$;

$$r0=\Delta/(6E-05\phi_{min}^4+0.0196\phi_{min}^3+2.2587\phi_{min}^2+125.58\phi_{min}+3046)$$

for $(1.68<r_0/\Delta<20)$; and $$r0=\Delta/(2E-06\phi_{min}^5+0.0007\phi_{min}^4+0.0947\phi_{min}^3+6.8299\phi_{min}^2+261.57\phi_{min}+4627.7)$$

for $(1.68<r_0/\Delta<100)$
wherein $\Delta$ is the thickness of the standard member 1, in μm.

FIG. 7 show phase shift simulation results for a standard member 1 with a thermal diffusivity $a=10^{-5}$ m²/s and a thickness $\Delta$ of 300 μm, for different r0/$\Delta$ ratios.

It is seen that in FIG. 7, in the case of an aforementioned ratio equal to 1 (FIG. 7(a)), there is no minimum for the sensitivity coefficients Xφ,kc and Xφ,cc$\rho$c. The occurrence of extrema independent of diffusivity begins from the ratio r0/$\Delta$≈1.5 (FIG. 7(b)). When the value of the r0/$\Delta$ ratio continues to increase, the sensitivity of the minimum relatively to the thickness of the layer is lost and when the radius r0 becomes a hundred times greater than the thickness $\Delta$ (FIG. 7(f)) the extraction of the minimum becomes quasi-impossible. Therefore, one has the relationship $$1.5 \cdot \Delta \leq r0 \leq 20 \cdot \Delta.$$

As shown in FIG. 9, measurements were conducted for:
standard members with the shape of stainless steel sheets with thicknesses comprised between 100 and 400 μm (FIG. 9A);
a standard member with a shape of titanium plate, with a thickness equal to 1.3 mm (r0=2.07 mm) (FIG. 9B); and
a standard member with the shape of a tungsten plate, with a thickness equal to 1 mm (r0=2.07 mm) (FIG. 9C).

The areas with too high excitation frequencies should not, of course, be taken into account.

In all the cases of FIG. 9, the accuracy obtained on the measurement of the radius r0 is comprised between 2% and 10%, with a value generally comprised around 5%.

The invention claimed is:

1. A system for measuring a radius r0 of a radiation beam, the system comprising:
   a source of a radiation beam configured for periodically exciting via heat a standard member in order to obtain a periodic thermal excitation of the standard member, the source of radiation beam being a laser or laser diode;
   an optical or acoustic sensor configured for measuring a periodic thermal response from the standard member, in response to the periodic thermal excitation;
   a processor configured for determining a phase shift between the periodic thermal excitation and the periodic thermal response for each frequency of a plurality of frequencies, determining a minimum $\phi_{min}$ of the determined phase shift, and determining the radius r0 of the radiation beam with a formula as follows:

$$r0=\Delta/g(\phi_{min})$$

wherein $\Delta$ is the thickness of the standard member, and
   g is a function which depends on the type of the radiation beam, and
   $\phi_{min}$ is a minimum of a plurality of the determined phase shifts.

2. The system according to claim 1, wherein the function g is polynomial, the coefficients of the polynomial depending on the heat radiation beam type.

3. The system according to claim 2, wherein, when the heat radiation beam is Gaussian, the processor is configured to determine the radius r0 of the beam, in mm, with the formula:

$$r0=(100 \cdot \Delta)/(0.227 \cdot \phi_{min}^3+57.856 \cdot \phi_{min}^2+5688.2 \cdot \phi_{min}+208620)$$

wherein $\Delta$ is the thickness of the standard member, in μm.

4. The system according to claim 1, wherein, when the heat radiation beam is uniform, the processor is configured to determine the radius r0 of the beam, in mm, with the formula:

$$r0=\Delta/(0.0032\phi_{min}^3+0.7405\phi_{min}^2+64.894\phi_{min}+2163.3)$$

for $(1.68<r_0/\Delta<10)$;

$$r0=\Delta/(6E-05\phi_{min}^4+0.0196\phi_{min}^3+2.2587\phi_{min}^2+125.58\phi_{min}+3046)$$

for $(1.68<r_0/\Delta<20)$; and $$r0=\Delta/(2E-06\phi_{min}^5+0.0007\phi_{min}^4+0.0947\phi_{min}^3+6.8299\phi_{min}^2+261.57\phi_{min}+4627.7)$$

for $(1.68<r_0/\Delta<100)$
wherein $\Delta$ is the thickness of the standard member, in μm.

5. The system according to claim 1, wherein the source is configured to excite the standard member in a sinusoidal periodic manner.

6. The system according to claim 1, wherein one has the relationship:

$$1.5 \cdot \Delta \leq r0 \leq 20 \cdot \Delta.$$

* * * * *